US012770722B2

(12) United States Patent
Chow et al.

(10) Patent No.: US 12,770,722 B2
(45) Date of Patent: Oct. 20, 2026

(54) METHOD FOR PREDICTING A SUITABLE THERAPY

(71) Applicants: National University of Singapore, Singapore (SG); National University Hospital (Singapore) PTE LTD, Singapore (SG); Kyan Therapeutics, Singapore (SG)

(72) Inventors: Edward Kai-Hua Chow, Singapore (SG); Wee Joo Chng, Singapore (SG); Anand Devaprasath Jeyasekharan, Singapore (SG); Sanjay De Mel, Singapore (SG); Masturah Mohd Abdul Rashid, Singapore (SG)

(73) Assignees: ASSIGNEENational University of Singapore, Singapore (SG); National University Hospital (Singapore) PTE LTD, Singapore (SG); Kyan Therapeutics Pte Ltd, Singapore (SG)

( * ) Notice: Subject to any disclaimer, the term of this patent is extended or adjusted under 35 U.S.C. 154(b) by 1221 days.

(21) Appl. No.: 17/769,954

(22) PCT Filed: Oct. 16, 2020

(86) PCT No.: PCT/SG2020/050595

§ 371 (c)(1),
(2) Date: Apr. 18, 2022

(87) PCT Pub. No.: WO2021/076058

PCT Pub. Date: Apr. 22, 2021

(65) Prior Publication Data

US 2022/0367023 A1 Nov. 17, 2022

(30) Foreign Application Priority Data

Oct. 18, 2019 (SG) ........................... 10201909760Q

(51) Int. Cl.
*G16H 20/10* (2018.01)
*G16C 20/30* (2019.01)
*G16H 10/40* (2018.01)

(52) U.S. Cl.
CPC ............. *G16H 20/10* (2018.01); *G16C 20/30* (2019.02); *G16H 10/40* (2018.01)

(58) Field of Classification Search
CPC ......... G16H 20/10; G16H 10/40; G16C 20/30
See application file for complete search history.

(56) References Cited

U.S. PATENT DOCUMENTS

2015/0356269 A1* 12/2015 Ho .......................... G06F 17/11 703/11
2019/0030026 A1 1/2019 Ho et al.

(Continued)

FOREIGN PATENT DOCUMENTS

WO 2016/179306 A1 11/2016

OTHER PUBLICATIONS

Zhou, Yong-Dao, and Hongquan Xu. "Composite designs based on orthogonal arrays and definitive screening designs." Journal of the American Statistical Association 112.520 (2017): 1675-1683. (Year: 2017).*

Zhang, Ting, et al. "Orthogonal array composite design to study and optimize antioxidant combinations in the prevention of UVB-induced HSF damage." Journal of Photochemistry and Photobiology B: Biology 178 (2018): 568-576. (Year: 2018).*

(Continued)

*Primary Examiner* — Jesse P Frumkin
(74) *Attorney, Agent, or Firm* — Patrick M. Torre; Stites & Harbison PLLC

(57) ABSTRACT

The invention relates to a method for predicting, selecting and screening a personalised combinatorial therapy for a patient comprising the steps of measuring a response output for each drug candidate in a sample obtained from the patient; determining a minimum set of test combinatorial therapies according to a composite experimental design, such as an orthogonal array composite design; measuring a (Continued)

response output and determining a relationship between the response output and the corresponding predetermined doses of the candidate drugs; and consequently deriving an optimal drug-dose combination for treating the patient.

17 Claims, 4 Drawing Sheets

(56) References Cited

U.S. PATENT DOCUMENTS

2021/0358636 A1* 11/2021 Ho .......................... G06F 17/11
2022/0373535 A1* 11/2022 Nowak-Sliwinska ....................... A61K 31/167

OTHER PUBLICATIONS

Ding, Xianting, et al. "Discovery of a low order drug-cell response surface for applications in personalized medicine." Physical biology 11.6 (2014): 065003. (Year: 2014).*

Weiss, Andrea, et al. "Rapid optimization of drug combinations for the optimal angiostatic treatment of cancer." Angiogenesis 18.3 (2015): 233-244. (Year: 2015).*

Notification of Transmittal of the International Search Report and the Written Opinion of the International Searching Authority, or the Declaration, Int'l Application No. PCT/SG2020/050595, mailed Jan. 26, 2021, 10 pages.

Rashid et al., Optimizing Drug Combinations against Multiple Myeloma Using a Quadratic Phenotypic Optimization Platform (QPOP), Sci Transl Med., Aug. 8, 2018, vol. 10, No. 453, pp. 1-17.

* cited by examiner

A

Top ranked single, 2- and 3-drug combinations

| | H | L |
|---|---|---|
| **Bortezomib** | 0.0348 | 0.160 |
| **Panobinostat** | 0.341 | 0.451 |
| **Gemcitabine** | 0.789 | 0.838 |
| **Brentuximab** | 0.876 | 0.881 |
| **Fludarabine** | 0.760 | 0.823 |

| | HH | HL | LH | LL |
|---|---|---|---|---|
| Bortezomib + Panobinostat | 0.153 | 0.0689 | 0.0546 | 0.110 |
| Gemcitabine + Bortezomib | 0.0177 | 0.103 | 0.0262 | 0.131 |

| | HHH | HLH | HHL | LHH | LHL | LLH | HLL | LLL |
|---|---|---|---|---|---|---|---|---|
| Bretuximab + Bortezomib + Panobinostat | -0.0387 | -0.247 | -0.170 | 0.0573 | -0.119 | -0.151 | -0.211 | -0.161 |
| Fludarabine + Bortezomib + Panobinostat | 0.142 | -0.080 | 0.148 | -0.124 | -0.089 | -0.180 | -0.075 | -0.145 |

Dead | Normalized Cell Viability | Live

| | |
|---|---|
| L | Lower concentration (i.e. $IC_{15}$) |
| H | Higher concentration (i.e. $IC_{30}$) |

Forrest plot of top ranking combinations

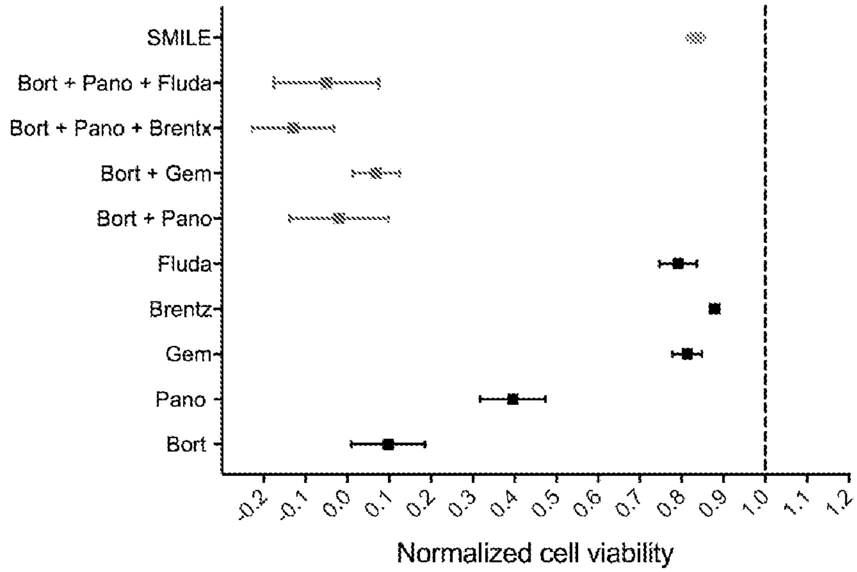

Figure 4

METHOD FOR PREDICTING A SUITABLE THERAPY

CROSS REFERENCE TO RELATED APPLICATIONS

This application is a U.S. National Phase Application of International Application No. PCT/SG2020/050595, filed Oct. 16, 2020, which claims the benefit of and priority to International application Ser. No. 10201909760Q filed Oct. 18, 2019, the entire disclosures of which are hereby incorporated by reference in their entirety for all purposes.

FIELD OF INVENTION

The invention relates generally to the field of clinical development. In particular, the invention relates to a method for predicting a suitable therapy for treating a patient.

BACKGROUND

Genomic heterogeneity, both inter-patient and intra-tumoral, contributes to the failure of targeted therapies as single agents. Combining targeted agents with each other and/or conventional chemotherapy partially alleviates this problem. However, there are no clinically approved methods for predicting the relative efficacy of combinations for individual patients. While companion diagnostics based on genomic sequencing have improved response rates to specific drugs, these targeted sequencing approaches do not account for uncharacterised genomic, epigenetic, metabolomic and proteomic factors that can affect therapeutic response. Network-modelling algorithms and pair-wise drug sensitivity algorithms improve patient subtype identification, however, these approaches still extrapolate individual responses from population-derived data.

Ex-vivo drug sensitivity experiments with primary patient tumor cells or patient-derived organoid and patient-derived xenografts potentially overcome the challenges to identifying appropriate therapies for individual patients. Given the range of anti-cancer drugs to choose from, methods for identifying personalised drug combinations require analysis of multiple combinations. In order to identify and rank drug combinations from a set of 12 drugs over a range of 3 concentrations, traditional high-throughput screening would have to test $3^{12}$ or 531,441 combinations. This number of combinations is incompatible with personalised clinical decision support, where patient-derived tumor cells are of limited quantity.

Accordingly, it is generally desirable to overcome or ameliorate one or more of the above mentioned difficulties.

SUMMARY

The present disclosure teaches a method for predicting a suitable therapy for treating a patient. Disclosed is a method for predicting a suitable therapy for treating a patient, the method comprising:

a) measuring a response output for each candidate drug from an initial set of candidate drugs in a sample obtained from the patient at one or more predetermined doses of the candidate drug;

b) determining a minimum set of test combinatorial therapies from the initial set of candidate drugs; wherein each test combinatorial therapy comprises zero, one or more candidate drugs at predetermined doses; wherein the minimum set of test combinatorial therapies is determined according to a composite experimental design;

c) measuring a response output for each test combinatorial therapy in the set in a sample obtained from the patient to determine a relationship between the response output and the predetermined doses of the corresponding candidate drugs, the relationship including one or more components indicative of respective drug-drug interactions; and d) predicting a suitable therapy for treating the patient based on the derived relationship.

Disclosed herein is a method for selecting a suitable therapy for treating a patient, the method comprising:

a) measuring a response output for each candidate drug from an initial set of candidate drugs in a sample obtained from the patient at one or more predetermined doses of the candidate drug;

b) determining a minimum set of test combinatorial therapies from the initial set of candidate drugs; wherein each test combinatorial therapy comprises zero, one or more candidate drugs at predetermined doses; wherein the minimum set of test combinatorial therapies is determined according to a composite experimental design;

c) measuring a response output for each test combinatorial therapy in the set in a sample obtained from the patient to determine a relationship between the response output and the corresponding predetermined doses of the candidate drugs, the relationship including one or more components indicative of respective drug-drug interactions; and d) selecting a suitable therapy for treating the patient based on the derived relationship.

Disclosed herein is a method for screening a drug combination for treating a patient, the method comprises:

a) measuring a response output for each candidate drug from an initial list of candidate drugs in a sample obtained from the patient at one or more predetermined doses of the candidate drug;

b) determining a minimum set of test combinatorial therapies from the initial set of candidate drugs; wherein each test combinatorial therapy comprises zero, one or more candidate drugs at predetermined doses; wherein the minimum set of test combinatorial therapies is determined according to a composite experimental design;

c) measuring a response output for each test combinatorial therapy in the set in a sample obtained from the patient to determine a relationship between the response output and the corresponding predetermined doses of the candidate drugs, the relationship including one or more components indicative of respective drug-drug interactions; and e) selecting a drug combination for treating the patient based on the derived relationship.

Disclosed herein is a method of treating a patient, the method comprising:

a) measuring a response output for each candidate drug from an initial list of candidate drugs in a sample obtained from the patient at one or more predetermined doses of the candidate drug;

b) determining a minimum set of test combinatorial therapies from the initial set of candidate drugs; wherein each test combinatorial therapy comprises zero, one or more candidate drugs at predetermined doses; wherein the minimum set of test combinatorial therapies is determined according to a composite experimental design;

c) measuring a response output for each test combinatorial therapy in the set in a sample obtained from the patient to determine a relationship between the response output and the corresponding predetermined doses of the candidate drugs, the relationship including one or more components indicative of respective drug-drug interactions;

d) selecting a suitable therapy for treating the patient from the minimum set of test combinatorial therapies based on the derived relationship; and e) treating the patient with the therapy.

BRIEF DESCRIPTION OF DRAWINGS

Embodiments of the present invention are hereafter described, by way of non-limiting example only, with reference to the accompanying drawings in which:

FIG. 4. Predictive output heat maps for patient-specific drug combination prioritization. Single-drug, 2-drug and 3-drug combination predicted output heat maps for top ranked drug combinations compared to forest plot of top ranked drug combinations versus standard of care SMILE.

DETAILED DESCRIPTION

Figure 1:
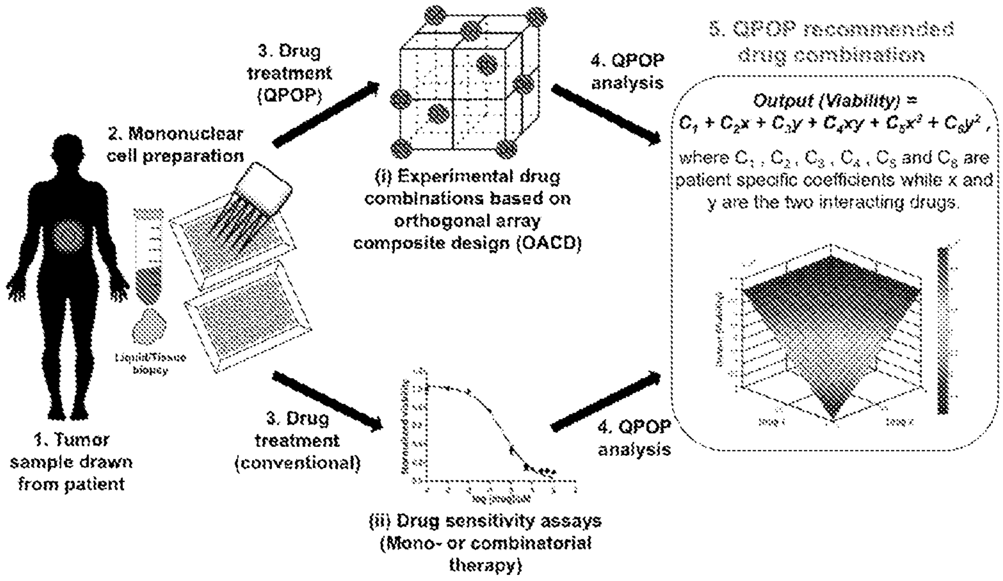
FIG. 1. Overview of the Quadratic Phenotypic Optimisation Platform (QPOP) process. Blood or tissue biopsy is obtained from patient (Step 1) and the tumor cells are isolated for downstream experiments. The cells are plated in 384-well plates (Step 2) before undergoing drug treatment (Step 3). This comprises of either a QPOP-specific drug combinatorial treatment (Step 3*i*) or the traditional serial dose response assays (Step 3*ii*). The data from steps 3*i* and 3*ii* are subjected to QPOP analyses (Step 4). Based on the coefficients derived from the QPOP analyses, QPOP highlights the most optimal patient-specific drug combinations and projects the 2-drug interactions via response surface maps, which aids in clinicians' decision-making.

The disclosure teaches a method for predicting a suitable therapy for treating a patient. Disclosed herein is a method for predicting a suitable therapy for treating a patient, the method comprising:

a) measuring a response output for each candidate drug from an initial list of candidate drugs in a sample obtained from the patient at one or more predetermined doses of the candidate drug;

b) determining a minimum set of test combinatorial therapies from the initial set of candidate drugs; wherein each test combinatorial therapy comprises zero, one or more candidate drugs at predetermined doses; wherein the minimum set of test combinatorial therapies is determined according to a composite experimental design;

c) measuring a response output for each test combinatorial therapy in the set in a sample obtained from the patient to determine a relationship between the response output and the predetermined doses of the candidate drugs, the relationship including one or more components indicative of respective drug-drug interactions; and d) predicting a suitable therapy for treating the patient based on the derived relationship.

The method may comprise selecting an initial list of candidate drugs.

The method may comprise a) measuring a response output for each candidate drug from an initial list of candidate drugs in a sample obtained from the patient at one or more predetermined doses of the candidate drug.

In one embodiment, the candidate drugs are clinically approved drugs. The initial set of candidate drugs may be clinically approved drugs which are known to be effective in treating the patient or are clinically approved drugs which are recommended by a physician, for that or other alternative diseases. The candidate drugs may also include investigational drugs. In one embodiment, the candidate drugs include clinically approved drugs and investigational drugs.

In one embodiment, the candidate drugs are anti-cancer drugs, which encompass but are not limited to the following classes of drugs: alkylating agents, antimetabolites, antibiotics, taxanes, alkaloids, microtubule inhibitors, targeted therapies, topoisomerase inhibitors, anti-hormonal agents, immunomodulators, bipshosphonates, anti-angiogenic inhibitors, monoclonal antibodies, PARP inhibitors, protein kinase inhibitors, proteasomal inhibitors, growth factor receptor inhibitors and epigenetic inhibitors. Such drugs include:

(i) alkylating agents, such as Cyclophosphamide (Cyclo), cis-platinum(II)-diaminedichloride (platinol or cisplatin); oxaliplatin (Eloxatin or Oxaliplatin Medac); and carboplatin (Paraplatin);

(ii) antitumour antibiotics, including those selected from the group comprising anthracyclines, such as doxorubicin (Adriamycin, Rubex);

(iii) antimetabolites, including folic acid analogues such as pyrimidine analogues such as Cytarabine (Cyta), 5-fluorouracil (Fluoruracil, 5-FU), gemcitabine (Gemzar), or histone deacetylase inhibitors (HDI) for instance, Vorinostat (rINN);

(iv) natural alkaloids, including paclitaxel (Taxol);

(v) inhibitors of protein tyrosine kinases and/or serine/threonine kinases including Sorafenib (Nexavar), Erlotinib (Tarceva), Dasatanib (BMS-354825 or Sprycel).

The one or more candidate drugs, may comprise, but are not limited to the following drugs: Cyclophosphamide (Cyclo), Doxorubucin (Dox), Etoposide (Etop), Cytarabine (Cyta), Gemcitabine, Dexamethasone (Dex), Cisplatin (Cisp), Methotrexate (Metho), Ifosfamide (IFos), L-asparaginase (L-asp) and Bortezomib.

In one embodiment, the one or more candidate drugs is selected from the group consisting of, Cyclophosphamide (Cyclo), Doxorubucin (Dox), Etoposide (Etop), Cytarabine (Cyta), Gemcitabine, Dexamethasone (Dex), Cisplatin (Cisp), Methotrexate (Metho), Ifosfamide (IFos), L-asparaginase (L-asp) and Bortezomib.

In one embodiment, the one or more candidate drugs is selected from the group consisting of gemcitabine, oxaliplatin, L-asparaginase, methotrexate, dexamethasone, etoposide, brentuximab, bortezomib, panobinostate, doxorubicin, cyclophosphamide and fludarabine.

In one embodiment, the predetermined doses are doses below clinically approved doses. This may involve determining the PK max concentration that is observed from the clinically approved doses and using this concentration as an upper limit threshold. The pre-determined dose of a candidate drug can be zero such that the candidate drug is absent in the test combinatorial therapy.

The response output for each candidate drug in a sample can be any quantifiable biological readout that includes, but is not limited to, high-content imaging based outputs (e.g. calcein AM, PI, pre-labelled cells, ATP-based cell viability assays), metabolic outputs (MTT/MTS), disease-specific markers (eg. FLC ratio, IFN-g), or cell signaling-specific outputs (eg., Wnt-activity, NFkb, etc.). The quantifiable biological readout may measure cell viability, cell numbers, apoptotic or dead cells, or population of cells undergoing cell cycle arrest.

The term "sample" may refer to any biological sample derived from an individual containing one or more cells. In one embodiment, the sample comprises one or more live cells. The sample may be blood, tissue, cell sample, organ or a biopsy.

In one embodiment, the "sample" is a "cancer sample". The term "cancer sample" may refer to any biological sample derived from an individual containing one or more cancer cells. In one embodiment, the cancer sample comprises one or more live cancer cells. The cancer sample may be blood, tissue, cell sample, organ or a biopsy. The biological sample may be a cancer cell line or organoid that is derived from a patient.

In one embodiment, the method comprises the ex vivo treatment of primary cells from a patient (such as primary tumor cells) and measurement of response output. The method may comprise assaying the primary cells ex vivo using microfluidics or nanowell formats to reduce on the number of cells required for testing.

The method may comprise b) determining a minimum set of test combinatorial therapies from the initial set of candidate drugs; wherein each test combinatorial therapy comprises zero, one or more candidate drugs at predetermined doses; wherein the minimum set of test combinatorial therapies is determined according to a composite experimental design.

The minimum set of test combination therapies may comprise at least one test combination therapy with no drug or one or more candidate drugs (such as two, three or more candidate drugs).

In one embodiment, the method comprises b) determining a minimum set of test combinatorial therapies from the initial set of candidate drugs; wherein each test combinatorial therapy comprises one or more candidate drugs at predetermined doses; wherein the minimum set of test combinatorial therapies is determined according to a composite experimental design.

In one embodiment, the test combination therapies comprises at least one monotherapy. In one embodiment, the test combination therapies comprises at least one 2 drugs combination. In one embodiment, the test combination therapies comprises at least one 3 drugs combination. In one embodiment, the test combination therapies comprises at least one 4 drugs combination. In one embodiment, the test combination therapies comprises at least one 5 drugs combination.

The minimum set of test combination therapies may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more test combination therapies.

In one embodiment, the composite experimental design is an orthogonal array composite design (OACD).

The OACD may comprise of the minimum number of designed experimental combinations for in depth screening analyses. This design may combine a two-level factorial or fractional factorial design (resolution IV or V) and a three-level orthogonal array, which succinctly covers the estimation of linear, bilinear as well as quadratic terms. OACD is advantageous over other composite designs as it allows the use of resolution IV for factor screening, which requires lesser number of experimental points. OACD of resolution IV (OACDIV) is able to estimate the linear effects clearly from the bilinear effects while bilinear interactions are aliased with each other. In this method, OACDIV is sufficient to determine the test drug combinations necessary to accurately predict an optimized therapeutic regimen of one or more drugs and/or combinations thereof. OACD of resolution V (OACDV) can also be used, although it requires more test drug combinations and more patient cells. As such, this method represents a refined and efficient method for determining optimized patient-specific treatment regimens.

The method may comprise c) measuring a response output for each test combinatorial therapy in the set in a sample obtained from the patient to determine a relationship between the response output and the corresponding doses of the candidate drugs.

In one embodiment, the relationship between the response output and the corresponding doses of the candidate drugs in step c) is represented by the second order quadratic equation:

$$y=\beta_0+\beta_1x_1+\ldots+\beta_nx_n+\beta_{12}x_1x_2+\ldots+\beta_{mn}x_mx_n+\beta_{11}x_1^2+\ldots+\beta_{nn}x_n^2$$

where y represents the desired output, $x_n$ is the nth drug dose, $\beta_0$ is the intercept term, $\beta_n$ is the single-drug coefficient of the $n^{th}$ drug, $\beta_{mn}$ is the interaction coefficient between the $m^{th}$ and $n^{th}$ drugs, and $\beta_{nn}$ is the quadratic coefficient for the $n^{th}$ drug.

The method may comprise d) predicting a suitable therapy for treating the patient from the minimum set of test combinatorial therapies.

The method may provide clinical decision support by assisting a physician on a suitable therapy to treat a patient. The method may assist on a decision between a monotherapy or a combination therapy comprising two or more drugs. The method may also assist on the dose to be used for each drug in a monotherapy or combination therapy.

The term "combination" or "combination therapy" is not intended to imply that the drugs must be administered at the same time and/or formulated for delivery together, although these methods of delivery are within the scope described herein. The drugs in the combination can be administered sequentially or concurrently. The drugs or therapeutic protocol can be administered in any order. In general, each drug will be administered at a dose and/or on a time schedule determined for that drug. In will further be appreciated that the drugs utilized in this combination may be administered together or separately in different compositions.

In one embodiment, the patient is a cancer patient. Alternatively, the patient may be one suffering from an infectious disease, diabetes or heart disease.

The terms "cancer" and "cancerous" refer to or describe the physiological condition in mammals that is typically characterized in part by unregulated cell growth. As used herein, the term "cancer" refers to non-metastatic and metastatic cancers, including early stage and late stage cancers. By "non-metastatic" is meant a cancer that remains at the primary site and has not penetrated into the lymphatic or blood vessel system or to tissues other than the primary site. The term "metastatic cancer" refers to cancer that has spread or is capable of spreading from one part of the body to another. Generally, a non-metastatic cancer is any cancer that is a Stage 0, I, or II cancer, and occasionally a Stage III cancer. A metastatic cancer, on the other hand, is usually a stage IV cancer.

The term "cancer" includes but is not limited to, breast cancer, large intestinal cancer, lung cancer, small cell lung cancer, gastric (stomach) cancer, liver cancer, blood cancer, bone cancer, pancreatic cancer, skin cancer, head and/or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, Hodgkin's disease, non-Hodgkin's lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma (also known as intraocular melanoma), testicular cancer, oral cancer, pharyngeal cancer or a combination thereof.

In one embodiment, the cancer is a solid or haematological cancer.

The term "haematological cancer" may refer to one or more of leukemia, lymphoma, Chronic Myeloproliferative Disorders, Langerhans Cell Histiocytosis, Multiple Myeloma/Plasma Cell Neoplasm, Myelodysplasia Syndromes, Myelodysplastic/Myeloproliferative Neoplasms or a combination thereof. In some embodiments, leukemia is any one or more of Acute Lymphoblastic Leukemia (ALL), Acute Myeloid Leukemia (AML), Chronic Lymphocytic Leukemia (CLL), Chronic Myelogenous Leukemia (CML), Hairy Cell Leukemia (HCL) or a combination thereof. In some embodiments, lymphoma is any one or more of AIDS-Related Lymphoma, Cutaneous T-Cell Lymphoma, Hodgkin Lymphoma, Mycosis Fungoides, Non-Hodgkin Lymphoma, Primary Central Nervous System Lymphoma, Sezary Syndrome, T-Cell Lymphoma, Cutaneous, Waldenstrom Macroglobulinemia or a combination thereof.

The haematological cancer may be a leukemia or a lymphoma (such as a Hepatosplenic T-cell Lymphoma).

The term "solid cancer" may refer to one or more of breast cancer, large intestinal cancer, lung cancer, small cell lung cancer, gastric (stomach) cancer, liver cancer, bone cancer, pancreatic cancer, skin cancer, head and/or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, esophageal cancer, small intestine cancer, endocrine cancer, thyroid cancer, parathyroid cancer, adrenal cancer, soft tissue tumor, urethral cancer, penile cancer, prostate cancer, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma (also known as intraocular melanoma), testicular cancer, oral cancer, pharyngeal cancer, sarcomas or a combination thereof.

In one embodiment, the cancer is a metastatic cancer. The cancer may be a refractory or a relapsed cancer.

The term "treating" as used herein may refer to (1) preventing or delaying the appearance of one or more symptoms of the disorder; (2) inhibiting the development of the disorder or one or more symptoms of the disorder; (3) relieving the disorder, i.e., causing regression of the disorder or at least one or more symptoms of the disorder; and/or (4) causing a decrease in the severity of one or more symptoms of the disorder.

The terms "patient", "subject", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the phylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. In one embodiment, the subject is human.

The term "administering" refers to contacting, applying or providing a therapy to a subject.

In one embodiment, the therapy is a personalized therapy.

Provided herein is a suitable therapy as identified according to a method as defined herein. In one embodiment, the method further comprise treating the patient.

Disclosed herein is a method for selecting a suitable therapy for treating a patient, the method comprising:

a) measuring a response output for each candidate drug from an initial list of candidate drugs in a sample obtained from the patient at one or more predetermined doses of the candidate drug;
b) determining a minimum set of test combinatorial therapies from the initial set of candidate drugs; wherein each test combinatorial therapy comprises zero, one or more candidate drugs at predetermined doses; wherein the minimum set of test combinatorial therapies is determined according to a composite experimental design;
c) measuring a response output for each test combinatorial therapy in the set in a sample obtained from the patient to determine a relationship between the response output and the corresponding predetermined doses of the candidate drugs, the relationship including one or more components indicative of respective drug-drug interactions; and d) selecting suitable therapy for treating the patient based on the derived relationship.

Disclosed herein is a method for screening a drug combination for treating a patient, the method comprises:

a) measuring a response output for each candidate drug from a list of candidate drugs in a sample obtained from the patient at one or more predetermined doses of the candidate drug;

b) determining a minimum set of test combinatorial therapies from the initial set of candidate drugs; wherein each test combinatorial therapy comprises zero, one or more drugs at predetermined doses; wherein the minimum set of test combinatorial therapies is determined according to a composite experimental design;

c) measuring a response output for each test combinatorial therapy in the set in a sample obtained from the patient to determine a relationship between the response output and the corresponding predetermined doses of the candidate drugs, the relationship including one or more components indicative of respective drug-drug interactions; and d) selecting a drug combination for treating the patient based on the derived relationship of candidate drugs and candidate drug-drug interactions with patient-specific sample response.

Provided herein is a drug combination obtained according to a method as defined herein.

Provided herein is a pharmaceutical composition comprising a drug combination as defined herein and a pharmaceutically acceptable carrier.

By "pharmaceutically acceptable carrier" is meant a solid or liquid filler, diluent or encapsulating substance that can be safely used in topical or systemic administration to an animal, preferably a mammal, including humans. Representative pharmaceutically acceptable carriers include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient(s), its use in the pharmaceutical compositions is contemplated.

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Suitable dosage amounts and dosing regimens can be determined by the attending physician and may depend on the severity of the condition as well as the general age, health and weight of the patient to be treated. For example, the dosing schedule (such as the dosing schedule of each drug in a drug combination) can be altered during the course of treatment such that the dosage or frequency is increased or reduced during the course of treatment. The dosing schedule may also include breaks in administration.

In one embodiment, there is provided a method of treating a patient comprising administering the drug combination as defined herein to the patient.

In one embodiment, there is provided a drug combination as defined herein for use in the treatment of a patient in need thereof.

In one embodiment, there is provided the use of a drug combination as defined herein in the manufacture of a medicament for the treatment of a patient in need thereof.

Disclosed here is a method of treating a patient, the method comprising:

a) measuring a response output for each candidate drug from an initial list of candidate drugs in a sample obtained from the patient at one or more predetermined doses of the candidate drug;

b) determining a minimum set of test combinatorial therapies from the initial set of candidate drugs; wherein each test combinatorial therapy comprises zero, one or more drugs at predetermined doses; wherein the minimum set of test combinatorial therapies is determined according to a composite experimental design;

c) measuring a response output for each test combinatorial therapy in the set in a sample obtained from the patient to determine a relationship between the response output and the corresponding predetermined doses of the candidate drugs, the relationship including one or more components indicative of respective drug-drug interactions;

d) selecting suitable therapy for treating the patient based on the derived relationship; and e) treating the patient with the therapy.

In one embodiment, the method comprises administering the one or more drugs concurrently or sequentially to the patient.

Also disclosed is a method for selecting a patient for clinical trial studies. The method may comprise identifying patients that are more likely to respond to an investigational drug or investigational drug combination.

As used herein, "and/or" refers to and encompasses any and all possible combinations of one or more of the associated listed items, as well as the lack of combinations when interpreted in the alternative (or).

As used in this application, the singular form "a," "an," and "the" include plural references unless the context clearly dictates otherwise. For example, the term "an agent" includes a plurality of agents, including mixtures thereof.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Ex-vivo drug sensitivity experiments with primary patient tumor cells or patient-derived organoid and patient-derived xenografts potentially overcome the challenges to identifying appropriate therapies for individual patients. Given the range of anti-cancer drugs to choose from, methods for identifying personalised drug combinations require analysis of multiple combinations. In order to identify and rank drug combinations from a set of 12 drugs over a range of 3 concentrations, traditional high-throughput screening would have to test $3^{12}$ or 531,441 combinations. This number of combinations is incompatible with personalised clinical decision support, where patient-derived tumor cells are of limited quantity.

OACD

Tumor cells from an oncology patient sample are treated with a series of test drug combinations defined by Resolution IV Orthogonal Array Composite Design. This array of tests is used to derive coefficients for single drug and drug-drug interactions for all the drugs within the drug search set. These coefficients are used to calculate a predicted output of potential drug combinations (up to 4 drugs) from the drug search set. Patient-specific drug combinations are prioritized based on predicted output of single drug, 2-drug, 3-drug or 4-drug combinations. Based on this platform, patients can be treated with either monotherapy up to 4-drug therapy.

QPOP

The inventors have established a method of utilizing an adaptation of a Quadratic Phenotypic Optimisation Platform (QPOP) (Rashid M, Toh T B, Hooi L, et al. Optimizing drug combinations against multiple myeloma using a quadratic phenotypic optimization platform (QPOP). *Sci Transl Med.* 2018; 10(453)) towards oncology patient-specific drug combination optimization and prioritization (FIG. 1). In the current embodiment, primary patient sample that contains tumor cells, either from a blood sample or solid tumor biopsy, is collected. Tumor cells are isolated and seeded 2000 cells/well in Nunc™ 384-Well Clear Polystyrene Plates. In the examples used here, cell viability was performed using the CellTiter-Glo® Luminescent Cell Viability Assay following the manufacturer's instructions (Promega, Madison, WI, USA). However, any accurate quantifiable biological readout can be used for this method. This includes, but not limited to, high-content imaging based outputs (eg. calcein AM, PI, pre-labelled cells), metabolic outputs (MTT/MTS), disease-specific markers (eg. FLC ratio, IFN-g), or cell signaling-specific outputs (eg., Wnt-activity, NFkb, etc.). The drug candidates for the initial experiment comprised of standard regimens and active agents for T-cell lymphoma, chosen in consideration of the treatment history of the patient.

Datasets for analysis by QPOP are built by ex vivo treatment of primary patient tumor cells with a series of drug combinations determined by orthogonal array composite design (OACD) to use the least number of combinations sufficient for factor screening and in-depth analyses, in concentrations that are at or below clinically approved doses (max Pk conc.), Table 1. Other data that could be used include a suitable range of drug combinations and their corresponding concentrations that sufficiently represent the drug dosing space. In this example, a serial drug dose-response assays, with multiple concentrations of bortezomib, panobinostat, was also tested as either single or combinatorial treatments (100, 50, 25, 10, 5, 1, 0.1, 0.01, 0.001, 0.0001 μM). In these examples here, the viability of cells exposed to the various drug combinations are the phenotypic output which is analyzed by the QPOP assay. The correlation of treatment combination (input) and viability (output) was fitted into a second-order quadratic equation. The coefficients of the second-order equation represent the correlation between the input, drug dose of the drug combination, and the output cell viability, allowing for optimizing drug combination. In the analysis, each drug combination was represented as a vector and coded dosages were used in MATLAB. The second-order quadratic equation is as follows:

$$y=\beta_0+\beta_1x_1+\ldots+\beta_nx_n+\beta_{12}x_1x_2+\ldots+\beta_{mn}x_mx_n+\beta_{11}x_1^2+\ldots+\beta_{nn}x_n^2$$

where y represents the desired output, xn is the nth drug dosage, β0 is the intercept term, βn is the single-drug coefficient of the nth drug, βmn is the interaction coefficient between the mth and nth drugs, and βnn is the quadratic coefficient for the nth drug. To further validate and understand the top-ranked drug combination, a second-order quadratic fit response map for drug-drug interactions is made (FIG. 2A). The coefficients were calibrated using the data points in dose response assay of single drugs and drug combination (Table 2). To ensure the robustness and integrity of the assay, Z' score is calculated after every QPOP analysis.

TABLE 1

List of drugs and their corresponding concentrations used in the ex vivo QPOP experiment

| Drugs | $IC_0$ (μM) | $IC_{15}$ (μM) | $IC_{30}$ (μM) |
|---|---|---|---|
| Cyclophosphamide (Cyclo) | 0 | 30 | 60 |
| Doxorubicin (Dox) | 0 | 0.0225 | 0.045 |
| Etoposide (Etop) | 0 | 0.283 | 0.565 |
| Cytarabine (Cyta) | 0 | 0.233 | 0.466 |
| Gemcitabine (Gem) | 00 | 0.00779 | 0.0156 |
| Dexamethasone (Dex) | 0 | 0.06 | 0.12 |
| Cisplatin (Cisp) | 0 | 1.5 | 3 |
| Methotrexate (Metho) | 0 | 0.3 | 0.6 |
| Ifosfamide (Ifos) | 0 | 15 | 30 |
| L-asparaginase (L-asp) | 0 IU/ml | 0.3 IU/ml | 0.6 IU/ml |
| Bortezomib (Bort) | 0 | 0.006 | 0.012 |

TABLE 2

Estimates and significance from the ex vivo QPOP analysis of 11 drugs at 3 doses.

| | Estimate | SE | tStat | pValue |
|---|---|---|---|---|
| Intercept | 0.946023981 | 0.080018566 | 11.82255605 | 5.19E−22 |
| Doxorubicin | 4.894618147 | 1.259143163 | 3.887261029 | 0.000164809 |
| Etoposide | 2.296846109 | 0.598933677 | 3.83489224 | 0.000199505 |
| Cytarabine | −0.574132928 | 0.158711628 | −3.617459771 | 0.000432653 |
| Gemcitabine | 6.257947465 | 4.110517101 | 1.522423411 | 0.130469838 |
| Dexamethasone | 1.222365916 | 0.613581982 | 1.992180265 | 0.048565932 |
| Cisplatin | 0.061890049 | 0.110877984 | 0.558181585 | 0.577735015 |
| Methotrexate | −0.223684475 | 0.09475671 | −2.360618846 | 0.01981693 |
| Ifosfamide | −0.032628226 | 0.010976873 | −2.972451884 | 0.003555098 |
| L-asparaginase | −1.281827615 | 0.522933608 | −2.451224393 | 0.015642234 |
| Bortezomib | −82.00014241 | 27.59699835 | −2.971342802 | 0.003567088 |
| Doxorubicin:Cisplatin | −2.051178212 | 0.484043516 | −4.237590519 | 4.39E−05 |
| Doxorubicin:Bortezomib | −337.7553502 | 122.7259088 | −2.752111217 | 0.006817626 |
| Etoposide:Dexamethasone | −1.859881828 | 0.977154099 | −1.903365938 | 0.059329652 |
| Cytarabine:Gemcitabine | −15.17821989 | 8.920514418 | −1.701496033 | 0.091376391 |
| Cytarabine:Dexamethasone | −2.666401979 | 1.20842133 | −2.20651681 | 0.02920448 |
| Cytarabine:Methotrexate | 0.440907861 | 0.233939392 | 1.884709783 | 0.061828885 |

TABLE 2-continued

Estimates and significance from the ex vivo QPOP analysis of 11 drugs at 3 doses.

| | Estimate | SE | tStat | pValue |
|---|---|---|---|---|
| Cytarabine:Bortezomib | 32.75223994 | 11.78604544 | 2.778899854 | 0.006310836 |
| Gemcitabine:Methotrexate | −13.95018225 | 6.928141704 | −2.01355325 | 0.046238913 |
| Gemcitabine:Ifosfamide | 0.29274016 | 0.141293726 | 2.071855327 | 0.040368922 |
| Dexamethasone:Cisplatin | 0.402256926 | 0.184736867 | 2.177458857 | 0.031355123 |
| Dexamethasone:Bortezomib | −77.34699145 | 46.18421663 | −1.674749451 | 0.09652415 |
| Cisplatin:L-asparaginase | −0.07316343 | 0.036817773 | −1.987176975 | 0.04912483 |
| Cisplatin:Bortezomib | 4.638045389 | 1.813588161 | 2.557386229 | 0.011761091 |
| $Etoposide^2$ | −3.738583012 | 1.048557784 | −3.565452537 | 0.000518239 |
| $Cisplatin^2$ | −0.067562704 | 0.035788232 | −1.887846937 | 0.061402556 |
| $Ifosfamide^2$ | 0.001005944 | 0.000361636 | 2.781648462 | 0.006260829 |
| $L\text{-}asparaginase^2$ | 2.237279089 | 0.862626376 | 2.593566752 | 0.010650918 |
| $Bortezomib^2$ | 5456.048086 | 2236.764482 | 2.439259086 | 0.016144448 |

Figure 2:
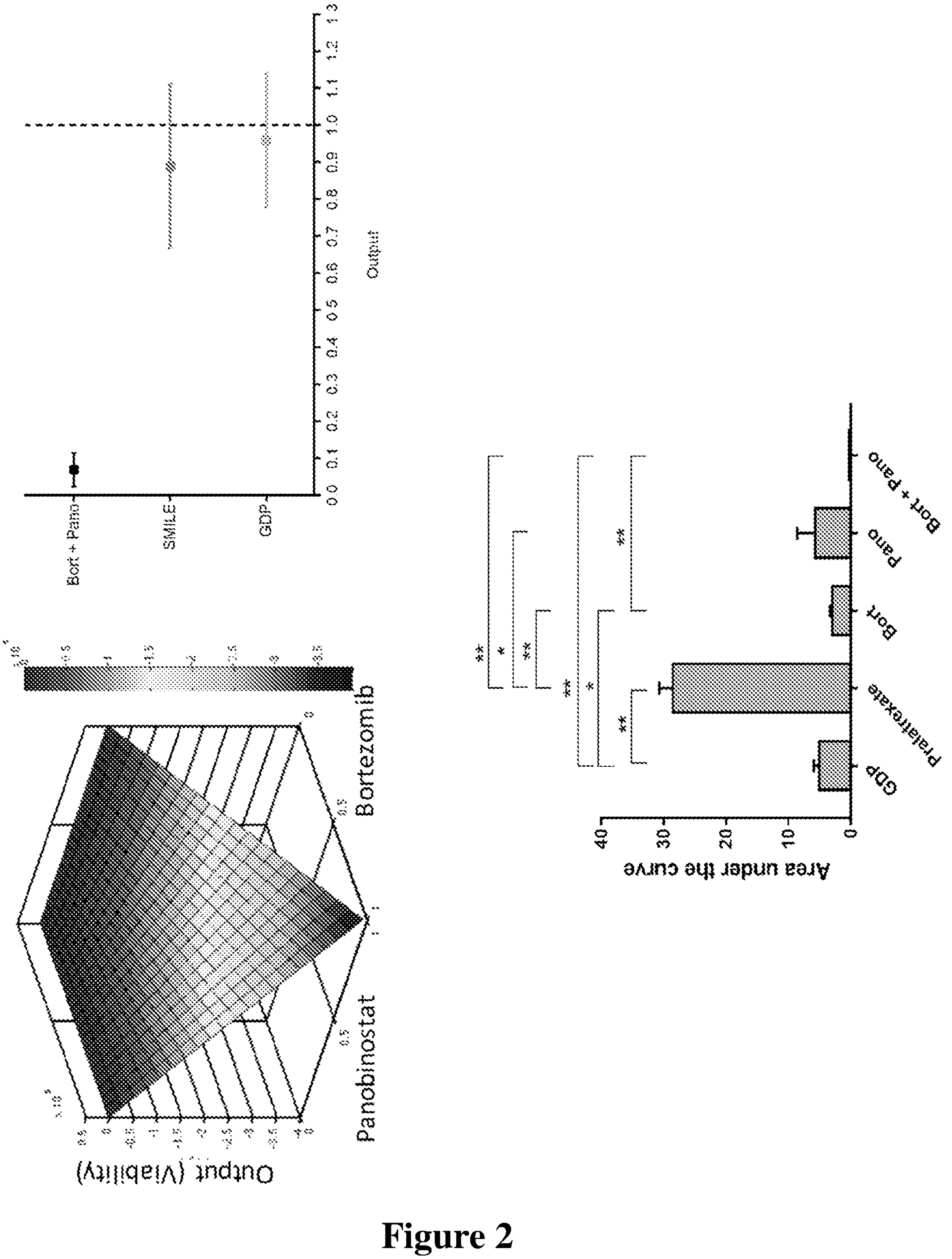
FIG. 2. QPOP-derived drug combination prioritization. (Upper Left) Response surface maps illustrating the interaction between BP and (Upper Right) forest plot comparing the projected outputs of QPOP analysis between BP as well as SMILE and GDP. (Lower Panel) Graphical comparison of the area under the dose response curves for Panobinostat and Bortezomib, for mono- and combinatorial therapy, against GDP and Pralatrexate in validation experiments comparing QPOP-derived versus standard of care. All bar plots represent means±SD, where *P<0.05 and **P<0.01. Statistical analyses were performed using two-tailed Student's t test.
Figure 3:
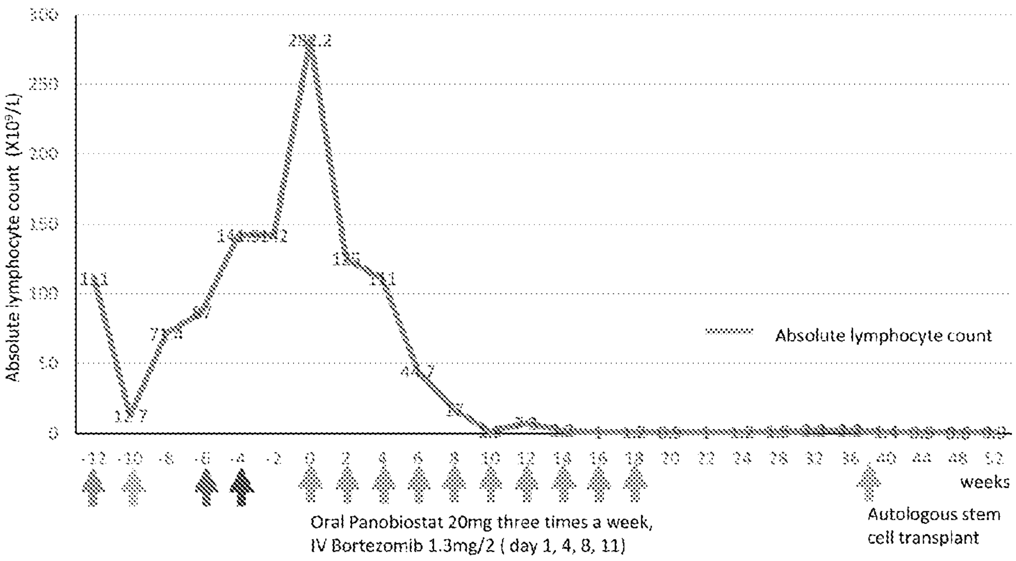
FIG. 3. Clinical Response to Treatment with BP. (A) The trend of the absolute lymphocyte count after treatment with each regimen. Colour coded arrows indicate treatment regimens given before bortezomib panabinostat (blue arrows). Orange: HyperCVAD B, Yellow: Pembrolizumab, Green: Gemcitabine, Vinorelbine, Liposomal Doxorubicin, Red: Pralatrexate. A rapid and sustained reduction of the ALC was seen after treatment with the BP regimen. This was accompanied by an improvement in haemoglobin and platelet count (data not shown).

Based on the derived coefficients, drug-drug interactions as well as comparable predictive outputs of top ranked drug combinations compared to standard of care regimens could be derived (Table 2, FIG. 2). The flexibility of QPOP is its ability to analyze drug combination data from multiple experimental designs of interrogated drug combinations. For the first ex vivo QPOP experiment, a specific design with the minimum number of drug combinations to accurately capture the entire drug dosing space was used. Inclusion of serial dose-response assay data from bortezomib and panobinostat allowed QPOP to analyze and rank the combination of bortezomib and panobinostat even though panobinostat was not initially included in original search set. From this analysis, a sharp decrease that culminates upon the blue regions as the concentrations increase was observed, suggesting a highly synergistic interaction (FIG. 2). Comparing against the earlier combinatorial outputs, Bortezomib and Panobinostat ranks as the best drug combination in the QPOP-derived forest plot from a selection of potential drug combinations (FIG. 2). When validated, the top ranked derived drug combination outperforms standard of care. By applying QPOP towards ex vivo drug combination sensitivity analysis of primary HSTCL cells from a patient, an actionable drug combination in bortezomib and panobinostat was identified within one week of sample collection. Concordance between QPOP analysis and patient response provides strong evidence that QPOP can be integrated into a clinical decision support system as an ex vivo drug combination sensitivity platform (FIG. 3).

Beyond drug combination rankings, the platform also provides additional data support towards prioritization of patient-specific single-drug, 2-drug and 3-drug combinations. Heat map comparison of predicted outcomes of single-drug, 2-drug and 3-drug combinations serve to provide further guidance for clinical decision support. In FIG. 4 for another patient sample, the predicted outcomes suggest single drug treatment with Bortezomib may be as effective as all of the 2-drug or 3-drug combinations, including except for Bortezomib+Panobinostat. Because of the relative similarity in predicted output, single drug treatment with Bortezomib can be suggested to the clinician so as to avoid additional toxicity risks from combination therapy. Heat maps clearly show that there is no clinical benefit to 3-drug combinations. In this patient samples, a 12-drug search set (gemcitabine, oxaliplatin, L-asparaginase, methotrexate, dexamethasone, etoposide, brentuximab, bortezomib, panobinostate, doxorubicin, cyclophosphamide and fludarabine) was interrogated by OACD-designed minimal set of test drug combinations and then analysed by QPOP.

Ex vivo drug sensitivity testing platforms that analyse primary patient tumor samples hold the promise of improving identification of appropriate therapies for specific patients. Previously platforms rely on comparative single-drug or pairwise-drug sensitivity from multiple tumour samples, sometimes combined with large scale genomic analysis to build pharmacogenomic models. These models are reliant on assumptions of the underlying molecular mechanisms contributing to drug response, which are derived from the population and are not specific to any single patient. While useful for developing diagnostic biomarkers for overall improved drug selection, these platforms do not identify optimal drug combinations from amongst a set of actionable drugs in a patient-specific manner Single patient ex vivo drug sensitivity predictors typically require large amounts of tumour sample to test adequate combinations to be of clinical use. QPOP was developed to improve on existing systems, based on the concept that quantifiable phenotypic drug dose-responses can be determined by a second-order algebraic equation. As such, patient sample responses to combinations of drugs that fit within either an orthogonal array composite design or serial dose-response assay can be used to derive patient-specific single drug and multi-drug sensitivity coefficients. These values succinctly describe tumor cell response to all potential monotherapy and drug combinations exclusively based on experimentally derived data, without a prior assumptions of mechanism. Even with limited quantity of clinical material, the quadratic function can be mapped onto response surface maps to aid in the understanding of optimal drug combinations as well as monotherapy. The ability of QPOP to quickly identify and rank all possible therapeutic options from a predefined drug search set (using a minimal amount of primary cells) overcome some of the hurdles limiting the implementation of ex vivo drug sensitivity platforms in patient-specific clinical decision support.

The invention claimed is:

1. A method for predicting a suitable therapy for treating a cancer patient, the method comprising:

a) measuring a response output for each anti-cancer candidate drug from an initial set of candidate anti-cancer drugs in an ex vivo sample obtained from the cancer patient at one or more predetermined doses below clinically approved doses of the candidate drug;

b) determining a minimum set of test combinatorial therapies from the initial set of candidate drugs; wherein each test combinatorial therapy comprises zero, one or more candidate drugs at predetermined doses below clinically approved doses; wherein the minimum set of test combinatorial therapies is determined according to a composite experimental design;

c) measuring a response output for each test combinatorial therapy in the set in the ex vivo sample or another ex vivo sample obtained from the cancer patient to determine a relationship between the response output and the corresponding predetermined doses below clinically approved doses of the candidate drugs, the relationship including one or more components indicative of respective drug-drug interactions;

d) predicting the suitable anti-cancer therapy for treating the cancer patient based on the derived relationship.

2. The method according to claim 1, wherein the composite experimental design is an orthogonal array composite design (OACD).

3. The method according to claim 2, wherein the composite experimental design is an OACD resolution IV design.

4. The method of any one of claims 1 to 3, wherein the candidate drugs are clinically approved drugs.

5. The method of claim 4, wherein the one or more candidate drugs are selected from the group consisting of Cyclophosphamide (Cyclo), Doxorubucin (Dox), Etoposide (Etop), Cytarabine (Cyta), Gemcitabine, Dexamethasone (Dex), Cisplatin (Cisp), Methotrexate (Metho), Ifosfamide (IFos), L-asparaginase (L-asp) and Bortezomib.

6. The method of claim 1, wherein the relationship between the response output and the corresponding predetermined doses of the one or more drugs in step c) is represented by the second order quadratic equation:

$$y=\beta_0+\beta_1x_1+\ldots+\beta_nx_n+\beta_{12}x_1x_2+\ldots+\beta_{mn}x_mx_n+\beta_{11}x_1^2+\ldots+\beta_{nn}x_n^2$$

where y represents the desired output, $x_n$ is the nth drug dose, $\beta_0$ is an intercept term, $\beta_n$ is a single-drug coefficient of the $n^{th}$ drug, $\beta_{mn}$ is an interaction coefficient between the $m^{th}$ and $n^{th}$ drugs such that $\beta_{mn}X_mX_n$ is one of said components indicative of a drug-drug interaction for the $m^{th}$ and $n^{th}$ drugs, and $\beta_{nn}$ is a quadratic coefficient for the $n^{th}$ drug.

7. The method of claim 1, wherein the cancer is a solid or haematological cancer.

8. The method of claim 1, wherein the therapy is a personalized therapy.

9. The method of claim 1, wherein the method further comprises treating the patient.

10. The method of claim 1, wherein the initial set of candidate anti-cancer drugs includes at least eleven candidate anti-cancer drugs.

11. A method for selecting a suitable anti-cancer therapy for treating a cancer patient, the method comprising:

a) measuring a response output for each anti-cancer candidate drug from an initial set of candidate anti-cancer drugs in an ex vivo sample obtained from the cancer patient at one or more predetermined doses below clinically approved doses of the candidate drug;

b) determining a minimum set of test combinatorial therapies from the initial set of candidate anti-cancer drugs; wherein each test combinatorial therapy comprises zero, one or more candidate anti-cancer drugs at predetermined doses below clinically approved doses; wherein the minimum set of test combinatorial therapies is determined according to a composite experimental design;

c) measuring a response output for each test combinatorial therapy in the set in the ex vivo sample or another ex vivo sample obtained from the cancer patient to determine a relationship between the response output and the corresponding predetermined doses of the candidate drugs below clinically approved doses, the relationship including one or more components indicative of respective drug-drug interactions; and d) selecting the suitable anti-cancer therapy for treating the cancer patient based on the derived relationship.

12. The method of claim 11, wherein the initial set of candidate anti-cancer drugs includes at least eleven candidate anti-cancer drugs.

13. A method for screening a drug combination for treating a cancer patient, the method comprises:

a) measuring a response output for each candidate anti-cancer drug from an initial set of candidate anti-cancer drugs in an ex vivo sample obtained from the cancer patient at one or more predetermined doses below clinically approved doses of the candidate drug;

b) determining a minimum set of test combinatorial anti-cancer therapies from the initial set of candidate drugs; wherein each test combinatorial therapy comprises zero, one or more candidate drugs at predetermined doses below clinically approved doses; wherein the minimum set of test combinatorial therapies is determined according to a composite experimental design;

c) measuring a response output for each test combinatorial therapy in the set in the ex vivo sample or another ex vivo sample obtained from the cancer patient to determine a relationship between the response output and the corresponding predetermined doses of the candidate drugs below clinically approved doses, the relationship including one or more components indicative of respective drug-drug interactions; and d) selecting the anti-cancer drug combination for treating the cancer patient based on the derived relationship.

14. The method of claim 13, wherein the initial set of candidate anti-cancer drugs includes at least eleven candidate anti-cancer drugs.

15. A method of treating a cancer patient, the method comprising:

a) measuring a response output for each candidate anti-cancer drug from an initial set of candidate anti-cancer drugs in an ex vivo sample obtained from the cancer patient at one or more predetermined doses below clinically ed doses of the candidate drug;

b) determining a minimum set of test combinatorial therapies from the initial set of candidate anti-cancer drugs; wherein each test combinatorial therapy comprises zero, one or more candidate drugs at predetermined doses below clinically approved doses; wherein the minimum set of test combinatorial therapies is determined according to a composite experimental design;

c) measuring a response output for each test combinatorial therapy in the set in the ex vivo sample or another ex vivo sample obtained from the cancer patient to determine a relationship between the response output and the corresponding predetermined doses of the candidate drugs below clinically approved doses, the relationship including one or more components indicative of respective drug-drug interactions;

d) selecting a suitable anti-cancer therapy for treating the cancer patient based on the derived relationship; and e) treating the cancer patient with the anti-cancer therapy.

16. The method of claim 15, wherein the method comprises administering the one or more drugs concurrently or sequentially to the patient.

17. The method of claim 15, wherein the initial set of candidate anti-cancer drugs includes at least eleven candidate anti-cancer drugs.

* * * * *